US007060036B2

(12) United States Patent
Bradley (10) Patent No.: US 7,060,036 B2
(45) Date of Patent: Jun. 13, 2006

(54) RESPIRATORY OXYGEN CONSUMPTION MEASURING DEVICE AND METHOD

(75) Inventor: Austen Peter Bradley, Lymm (GB)

(73) Assignee: Nutren Technology Limited, Lancashire (GB)

( * ) Notice: Subject to any disclaimer, the term of this patent is extended or adjusted under 35 U.S.C. 154(b) by 137 days.

(21) Appl. No.: 10/467,936

(22) PCT Filed: Jan. 28, 2002

(86) PCT No.: PCT/GB02/00355

§ 371 (c)(1),
(2), (4) Date: Dec. 11, 2003

(87) PCT Pub. No.: WO02/065934

PCT Pub. Date: Aug. 29, 2002

(65) Prior Publication Data

US 2004/0082871 A1    Apr. 29, 2004

(30) Foreign Application Priority Data

Feb. 16, 2001  (GB)  .................... 0103951.0

(51) Int. Cl.
*A61B 5/08* (2006.01)
*G01F 25/00* (2006.01)
*G01P 21/00* (2006.01)

(52) U.S. Cl. ............ 600/532; 600/538; 600/529; 73/1.23; 73/1.19; 73/1.16

(58) Field of Classification Search ............... 600/529, 600/531, 532, 533, 537, 538; 73/1.16, 1.19, 73/1.21, 1.23, 1.33, 1.34
See application file for complete search history.

(56) References Cited

U.S. PATENT DOCUMENTS

| 3,523,529 | A | | 8/1970 | Kissen | |
| 5,069,220 | A | * | 12/1991 | Casparie et al. | ............ 600/532 |
| 5,285,794 | A | * | 2/1994 | Lynch | ............ 600/532 |
| 6,126,613 | A | * | 10/2000 | Edwards et al. | ............ 600/539 |
| 6,402,697 | B1 | * | 6/2002 | Calkins et al. | ............ 600/532 |

FOREIGN PATENT DOCUMENTS

| GB | 975712 | 11/1964 |
| WO | WO 98/53732 | 12/1998 |
| WO | WO 99/39637 | 8/1999 |
| WO | WO 01/08554 | 2/2001 |

OTHER PUBLICATIONS

McNeill, G., MD, "The Oxylog oxygen consumption meter: a portable device for measurement of energy expenditure [1-3]", American Journal of Clinical Nutrition, vol. 45, No. 6, 1987, pp. 1415-1419.

* cited by examiner

*Primary Examiner*—Navin Natnithithadha
(74) *Attorney, Agent, or Firm*—Faegre & Benson LLP (57) ABSTRACT

A portable apparatus for calculating respiratory oxygen consumption comprising a housing having a fluid inlet, a flow sensor, mounted within the housing, an oxygen sensor and means for calculating the respiratory oxygen consumption using data obtained from the oxygen sensor and the flow sensor. The invention also relates to a method of calculating respiratory oxygen consumption.

26 Claims, 4 Drawing Sheets

RESPIRATORY OXYGEN CONSUMPTION MEASURING DEVICE AND METHOD

FIELD OF THE INVENTION

The present invention relates to methods of and apparatus for calculation of respiratory oxygen consumption, in particular, although not exclusively, to indirect calorimeters and methods of using the same.

BACKGROUND OF THE INVENTION

Techniques of calorimetry are used to study the energy of metabolism in humans and animals. Calorimetry is used, for example, for diagnosis of metabolic disorders and for calculating nutritional requirements of a subject. Calorimetric measurements can be made directly as a measure of heat loss of a subject. Alternatively, indirect measurements can be made of a chemical by-product of metabolism.

A useful measure for nutritionists and sports scientists when assessing the health and fitness of a subject is the volume of oxygen consumed at rest and during or after physical exertion.

Indirect calorimetry often involves measuring the amount of carbon dioxide exhaled by a subject, which can in turn be used to calculate the oxygen consumption of the subject.

U.S. Pat. No. 5,178,155 discloses an indirect calorimeter that comprises a carbon dioxide scrubber arranged to remove carbon dioxide from the exhaled gas and in some embodiments from the inhaled gas also. The volume of oxygen consumed can be calculated from the amount of carbon dioxide removed from the exhaled gas by the scrubber. The calorimeter of U.S. Pat. No. 5,178,155 also comprises two flow meters, the first being arranged to monitor the inhaled gas flow and the exhaled gas flow after removal of the carbon dioxide and the second being arranged to monitor the exhaled gas flow before removal of the carbon dioxide.

International patent application number PCT/US99/17553 discloses a method and apparatus for analysing respiratory gases to determine oxygen consumption for indirect calorimetry purposes as well as carbon dioxide production by measuring the mass and volume flow rate of inhaled and exhaled gas. The flow measurements are made using known ultrasonic pulse transit time techniques. The gas density may be determined using acoustic impedance, speed of sound or temperature related techniques. The method involves calculating the oxygen content in the inhaled and exhaled gas. In one embodiment of PCT/US99/17553 measurements are made on the exhaled gas flow only. In this case, it is necessary to be aware of the oxygen content of the inhaled gas.

International patent application number PCT/US98/05297 discloses a calorimeter comprising a flow meter and a capnometer to compute the difference between the inhaled gas volume and the volume of the exhaled gas less the carbon dioxide volume. The capnometer measures the concentration of exhaled carbon dioxide. The amount of carbon dioxide in the exhaled gas can then be subtracted from the total volume of exhaled gas to obtain a value for the volume of exhaled gas excluding carbon dioxide. A bidirectional flow mater is also used to measure the flow rate of the inhaled and exhaled gas.

International patent application number PCT/US91/04587 discloses a calorimeter comprising means to condition inhaled gas to a temperature and water vapour comparable with that of the exhaled gas, then the volume of inhaled gas is measured. Carbon dioxide is removed from the exhaled gas by passing the exhaled gas through a carbon dioxide scrubber and then its volume is measured. A single flow meter may be used to measure the volume of both the inhaled and exhaled gas.

All of the indirect calorimeters described above are complicated to manufacture and use. It is an aim of preferred embodiments of the present invention to provide an alternative method and apparatus for calculating respiratory oxygen consumption and to provide an alternative indirect calorimeter and method of using the same.

SUMMARY OF THE INVENTION

The present invention provides a portable apparatus for calculating respiratory oxygen consumption comprising a housing having a fluid inlet, a flow sensor mounted within the housing, an oxygen sensor and means for calculating respiratory oxygen consumption using data obtained from the oxygen sensor and the flow sensor.

By "portable apparatus" we mean an apparatus that is hand portable such that it can be carried and used by an individual and can be hand held in use.

Suitably, the apparatus is an indirect calorimeter.

Suitably, the housing is generally tubular. The tubular housing may have any suitable cross-sectional shape.

Preferably the flow sensor comprises a movable member, movable by air pressure effected thereupon, and a movement sensor associated with the movable member.

Suitably, movement of the movable member within the housing is effected by passing a fluid into the housing through the fluid inlet. Suitably, the fluid is a gas. Suitably, the gas is exhaled breath.

The movable member may be a rotatable member, such as a rotor or paddle wheel, for example.

Alternatively the movable member may be a plunger, slidably mounted with the housing.

Suitably, the plunger is arranged to move slidably along the length of the tubular housing.

Suitably, there is a substantially fluid tight contact between the periphery of the plunger and the interior surface of the housing. Suitably, the cross-sectional shape of the plunger corresponds with the cross-sectional shape of the interior of the tubular housing.

Suitably the oxygen sensor is mounted to the housing, preferably within the housing.

The oxygen sensor may comprise any suitable oxygen sensor. An example of a suitable oxygen sensor is an MOX-1™ sensor available from City Technology Limited of Portsmouth, England.

Suitably, when the movable member comprises a plunger the oxygen sensor is attached to an end of the plunger. Preferably, the oxygen sensor is attached to an end of the plunger that is nearest the fluid inlet.

The oxygen sensor may be either directly or indirectly attached to the surface of the movable member. Alternatively, or in addition the oxygen sensor may be embedded in the movable member.

Alternatively, or in addition the oxygen sensor may be separate from the movable member.

The movement sensor is, suitably, arranged to measure the speed of movement of the movable member during use of the apparatus according to the invention.

Any suitable movement sensor may be used. For example, the movement sensor may comprise one or more sensor switches. Suitable sensor switches include a slotted opto switch number 304-560 available from RS Components Limited of Corby, England.

Suitably, the movement sensor is attached, either directly or indirectly, to the movable member. Preferably, a movement sensor is embedded in the movable member.

The movement sensor may comprise a first switch located on the movable member and a second switch located on the housing.

If the movable member is a rotor or paddle wheel, there may be plurality of first switches, each mounted on a separate blade of the motor, and a second switch located on the housing.

Suitably, the apparatus for calculating respiratory oxygen consumption is arranged such that the movable member moves only a pre-set distance within the housing during use. Suitably, the movable member moves between a start position and an end position.

The apparatus for calculating respiratory oxygen consumption may further comprise a fluid outlet. Suitably, when the movable member is a plunger the fluid outlet is located adjacent the end position of the plunger. Suitably, the fluid outlet is positioned such that excess exhaled breath passes out of the housing through the fluid outlet once the plunger reaches the end position and does not cause continued movement of the plunger within the housing.

The apparatus may further comprise a collection chamber. The collection chamber may be in direct or indirect fluid flow communication with the fluid outlet. The collection chamber may comprise any suitable device, for example a bag or box. Suitably, the oxygen sensor is located in the collection chamber. Suitably the collection chamber forms part of the housing of the apparatus and is therefore integral with the housing.

If the movement sensor comprises a first switch located on the movable member and a second switch located in the housing, the second switch is suitably located adjacent the fluid outlet. Suitably, the second switch is located downstream of the fluid outlet relative to the fluid inlet. When the movable member is a plunger, suitably the second switch is located at the end position of the plunger.

When the movable member is a plunger the apparatus in accordance with the present invention may comprise means to return the plunger to the start position. Suitably, the apparatus comprises means to return the plunger to the start position after calculation of the respiratory oxygen consumption has been made. Any suitable means of returning the plunger to the start position may be used, for example a spring.

The fluid inlet is suitably arranged to allow ingress of exhaled breath from a subject using the apparatus into the apparatus. The fluid inlet may be provided by the end of the housing.

Suitably, apparatus in accordance with the present invention comprises a mouthpiece associated with the fluid inlet. The fluid inlet may be provided by the mouthpiece. Alternatively, the fluid inlet may be separate from the mouthpiece. If the mouthpiece is separate from the fluid inlet, the mouthpiece is suitably directly connected to the fluid inlet.

The apparatus according to the present invention may comprise an opening in the housing. Suitably, the opening provides for external fluid to be inhaled through the apparatus by the subject using the apparatus. The opening may be sealed by a one way valve, which valve allows fluid to be inhaled through the opening but prevents exhaled fluid from passing through the opening. Suitably, substantially no movement of the movable member occurs when fluid is inhaled through the opening by the subject. If the movable member is a plunger, suitably the opening is located between the fluid inlet and the end of the plunger when the plunger is located in the start position.

The apparatus in accordance with the present invention may comprise any suitable means for calculating the respiratory oxygen consumption. For example, the apparatus may comprise a computer or other electronic device for calculating the respiratory oxygen consumption. The means for calculating the respiratory oxygen consumption may be mounted on the housing of the apparatus or detachably connected to the housing.

The present invention further provides a method of calculating respiratory oxygen consumption comprising the following steps:

(a) passing an exhaled breath into a housing;
(b) measuring the fraction of oxygen in the exhaled breath using an oxygen sensor;
(c) measuring the time taken to exhale the breath using a flow sensor mounted within the housing; and
(d) calculating the oxygen consumption using the data obtained in steps b and c.

Suitably, step (a) comprises passing an exhaled breath of known value into the housing.

Suitably the flow sensor comprises a movable member associated with a movement sensor and step (a) comprises passing an exhaled breath into a housing to cause movement of a movable member.

Suitably, the method of calculating respiratory oxygen consumption is a method of indirect calorimetry.

The method of the present invention may be carried out using the portable apparatus of the present invention.

When the apparatus comprises a movable member, suitably the volume of the exhaled breath is calculated by measuring the extent of movement of the movable member.

When the movable member is a plunger, suitably the volume of the exhaled breath is calculated by measuring the distance moved by the plunger.

The range of movement of the movable member within the housing may be restricted to a pre-set distance.

Alternatively, movement of the movable member is not restricted but the movement sensor and the oxygen sensor are arranged to take measurements only during movement of the movable member over a restricted movement range.

In both cases, measurements are made using the oxygen sensor and the movement sensor only for the duration of exhalation of a known volume of breath.

The method may be repeated one or more times to obtain an average calculation of oxygen consumption. If the method is repeated one or more times, the results are suitably integrated to provide an average figure.

The apparatus of the present invention and the method of the present invention may use the following formula to calculate the respiratory oxygen consumption per breath exhaled:

$$VO_2 = K \times (F_iO_2 - F_eO_2) \times V \times (30/t) \times C \qquad \text{Formula I}$$

Where, $VO_2$ is the respiratory oxygen consumption of the subject $F_iO_2$ is the fraction of inhaled oxygen $F_eO_2$ is the fraction of exhaled oxygen V is the volume of the exhaled breath over which the measurements are taken t is the time taken to exhale the known volume of breath C is the constant calorific value for oxygen (approximately 5 kcal).

K is a constant allowing for calibration.

The fraction of inhaled oxygen can be calculated from the gas inhaled by the subject. For instance, if the subject inhaled atmospheric air, the fraction of inhaled oxygen can either be assumed to be the standard value of 20.94%, or the actual fraction of oxygen in the atmospheric air can be measured using any known technique.

The fraction of exhaled oxygen is measured using the oxygen sensor.

The volume of the exhaled breath can be measured by any suitable method. Suitably, when the apparatus comprises a movable member, the movable member moves a known extent within the housing and this distance is used to measure the volume of the exhaled breath in respect of which measurements are taken. If the oxygen sensor is attached to the surface of the movable member the volume calculation must take into account the volume reduction caused by the presence of the oxygen sensor.

Suitably, in use, the movable member is arranged in the housing at a start position at which a first switch of a movement sensor is spaced apart from a second switch of the movement sensor. When exhaled breath passes into the housing the movable member suitably moves towards the second switch. Preferably, the movement sensor takes a measurement during movement of the first sensor from its start position until the first sensor reaches the position of the second sensor. In this way, the movement sensor takes measurements only for the duration of exhalation of a breath.

During exhalation of the breath the oxygen sensor measures the fraction of molecular oxygen in the exhaled breath.

The data obtained from the oxygen sensor and the flow sensor may then be used to calculate the oxygen consumption of the subject per breath using Formula I.

If the apparatus in accordance with the present invention comprises electronic means to calculate the oxygen consumption, the oxygen sensor and the flow sensor suitably transmit the data obtained directly to the electronic calculation means by means of electronic signals.

Advantageously, the method and apparatus of the present invention can be used to provide information on the oxygen consumption of a subject, for example a human or an animal.

The apparatus and method of the present invention are advantageously easy to use. Furthermore, the apparatus of the present invention is simple to manufacture.

BRIEF DESCRIPTION OF THE DRAWINGS

The present invention will now be described, by way of example only, with reference to the following drawings, in which.

DESCRIPTION OF PREFERRED EMBODIMENTS

Figure 1:
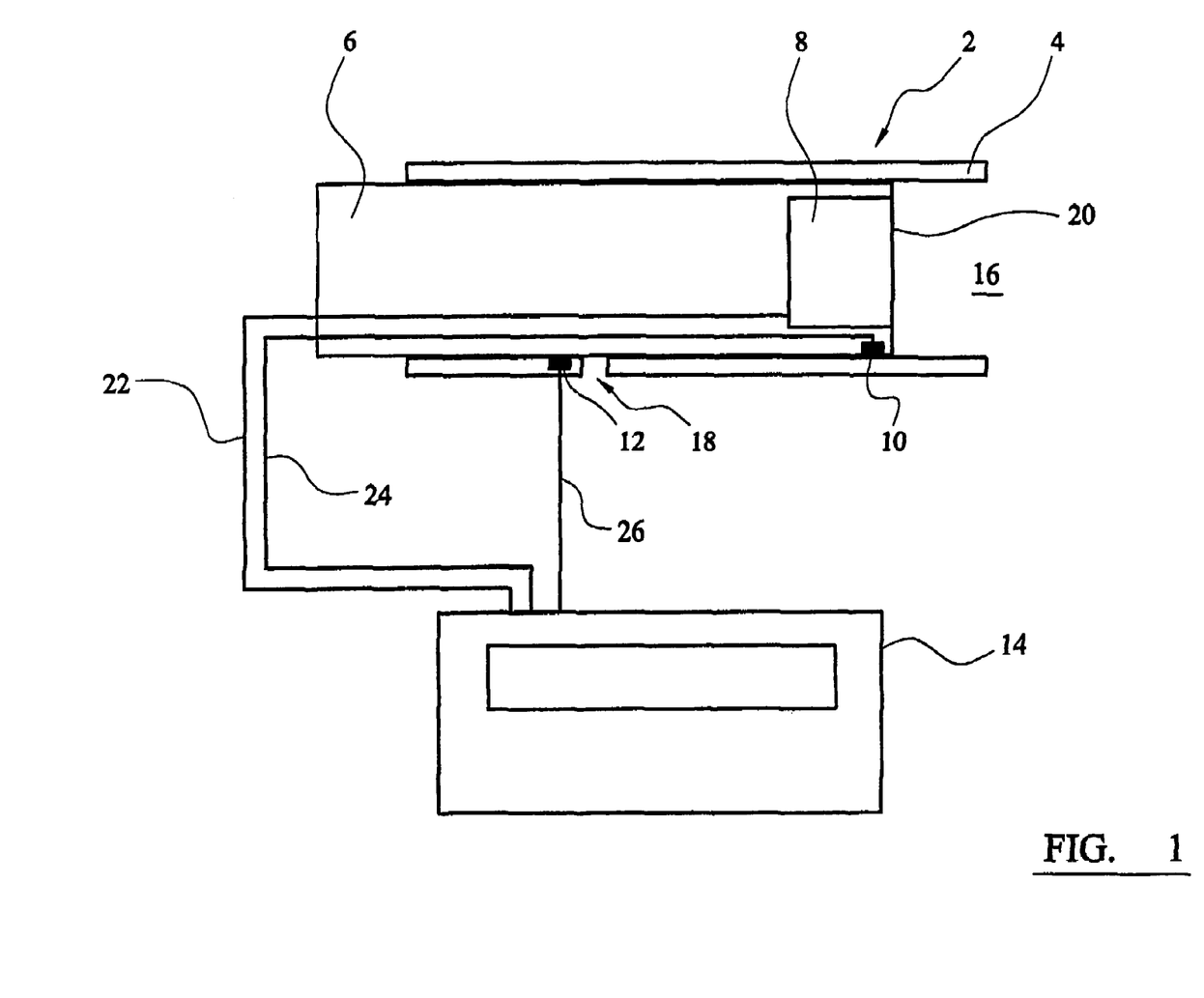
FIG. 1 is a schematic, partially cross sectional, side view of part of a portable apparatus in accordance with the present invention, in a start position.
Figure 2:
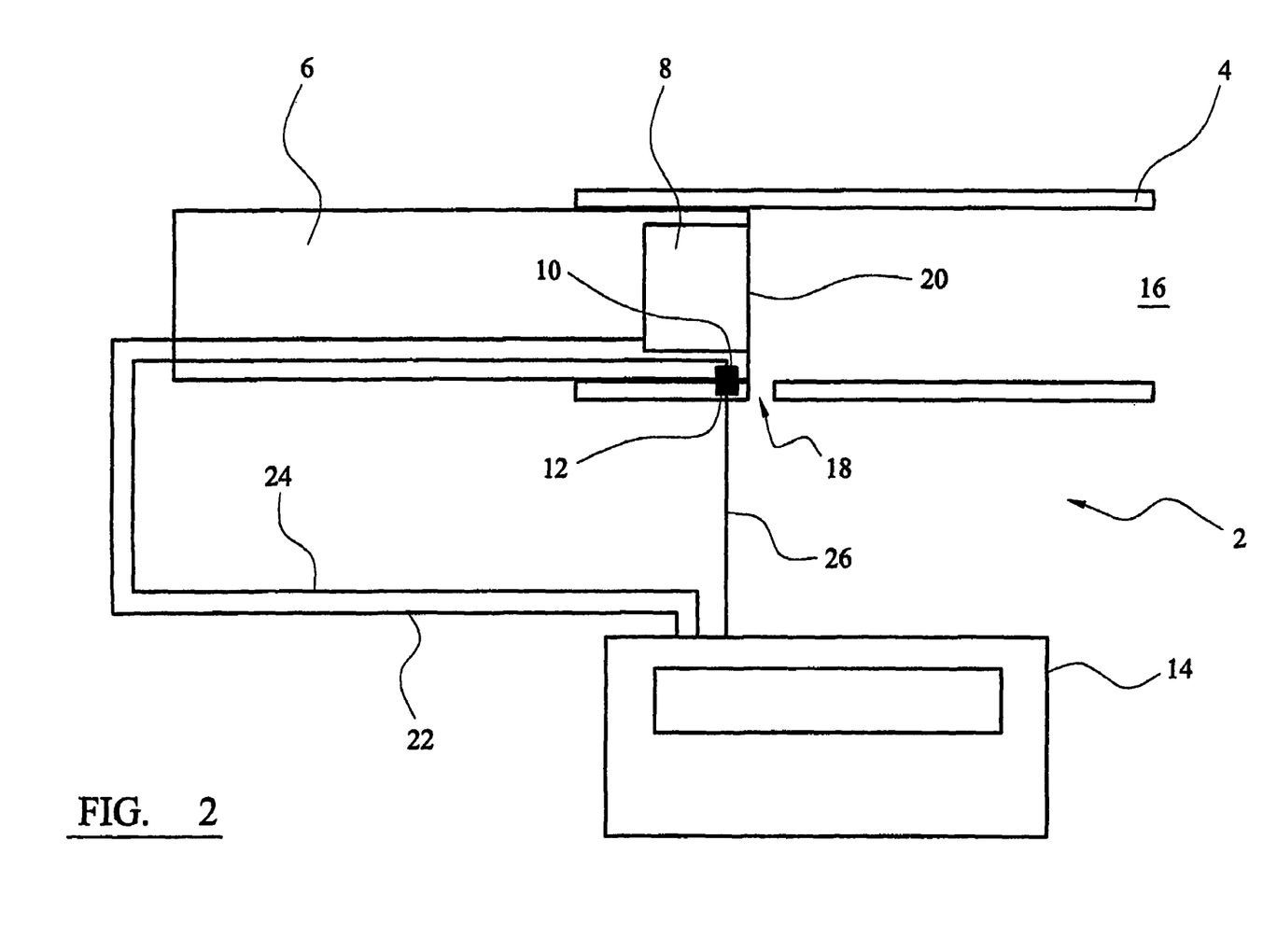
FIG. 2 is a schematic, partially cross-sectional, side view of the apparatus of FIG. 1 in an end position.

FIGS. 1 and 2 show part of a portable apparatus for calculating respiratory oxygen consumption 2 comprising a housing 4, a plunger 6, an oxygen sensor 8 and a movement sensor provided by a first switch 10 and a second switch 12. The apparatus 2 further comprises electronic calculation means 14.

The plunger 6 is slidably movable inside the housing 4, the interior of the housing 4 and the plunger 6 having the same cross-sectional shape. The relative dimensions of the periphery of the plunger 6 and the interior of the housing 4 being arranged such that there is a substantially fluid tight fit between the periphery of the plunger 6 and the interior of the housing 4.

The housing 4 comprises a fluid inlet 16 and a fluid outlet 18.

The oxygen sensor 8 is embedded in the end 20 of the plunger 6. The oxygen sensor is electrically connected to the electrical calculation means 14 by wire 22.

The first switch 10 of the movement sensor is embedded in a side of the plunger 4. The second switch 12 of the movement sensor is embedded in the interior wall of the housing 4. A wire 24 connects the first switch 10 with the electrical calculation means 14 and a wire 26 connects the second switch 12 with the electrical calculation means 14.

In use of the apparatus 2, the plunger 6 is arranged in the housing 4 at the start position as shown in FIG. 1. An exhaled breath is guided into the fluid inlet 16 of the housing 4. The end of the housing 4 providing the fluid inlet 16 may act as a mouthpiece for the apparatus 2. Alternatively, a separate mouthpiece (not shown) may be directly or indirectly connected to the housing 4.

The exhaled breath causes the plunger 6 to move away from the fluid inlet 16. The plunger 6 will continue to move in this direction until the end 20 of the plunger 6 passes the fluid outlet 18 to reach the end position as shown in FIG. 2. Thereafter, excess exhaled breath will pass out of the fluid outlet 18 and movement of the plunger 6 will cease.

Whilst the plunger 6 is moving from the start position to the end position, the oxygen sensor 8 is measuring the fraction of oxygen in the exhaled breath. The oxygen sensor 8 sends information of the measurement to the electrical calculation means 14 in the form of an electrical signal by means of wire 22.

During movement of the plunger 6 from the start position to the end position, the switches 10, 12 of the movement sensor measure the time taken to move this set distance. This time is a measurement of the time taken to exhale a known volume of breath. The switches 10, 12 send the measurement to the electrical calculation means 14 using wires 24 and 26.

The electrical calculation means 14 is programmed to calculate the oxygen consumption of the subject in accordance with Formula I set out above. In order to make this calculation the operator will need to insert details for the fraction of oxygen in the inhaled gas. This may be the standard value for the oxygen content of air, in this case, this information may be previously programmed into the electrical calculation means 14. If the oxygen fraction in the inhaled air is measured, the measured value will need to be input into the electrical calculation means 14 before the calculation can be made.

The method and calculation outlined above may be repeated one or more times, and the results may be integrated to provide an average value for the oxygen consumption.

The portable apparatus 2 is of a size and configuration such that it can be held and carried in the hand by an individual and connected to the electrical calculation means when desired.

Figure 3:
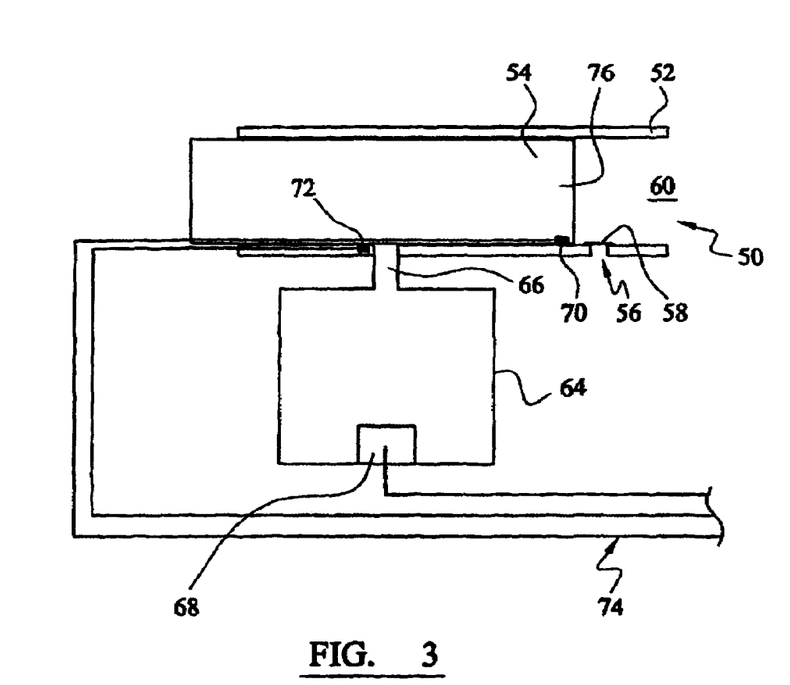
FIG. 3 is a schematic, partially cross-sectional, side view of a part of an alternative embodiment of a portable apparatus in according with the present invention, in a start position.
Figure 4:
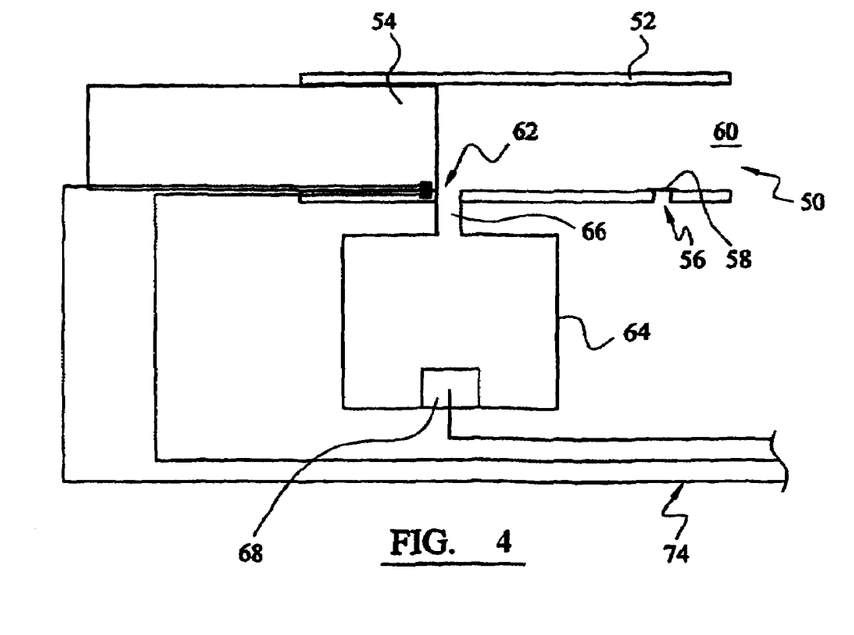
FIG. 4 is a schematic, partially cross-sectional, side view of the apparatus of FIG. 3 in an end position.

FIGS. 3 and 4 show part of an alternative portable apparatus for calculating respiratory oxygen consumption 50, comprising a housing 52 and a plunger 54.

The housing 52 comprises an opening 56 to allow ingress of external air. The opening 56 is covered by a one way valve 58, which valve 58 allows ingress through opening 56 of air but prevents egress of air through opening 56.

The housing 52 further comprises a fluid inlet 60 which allows inhaled external air to pass from the opening 56 to the subject (not shown) using the apparatus. The fluid inlet 60 also allows exhaled breath to pass into the housing 52.

The housing 52 also comprises a gas outlet 62, which allows exhaled breath to pass out of the housing 62. The gas outlet 62 is connected to a gas collection box 64 by means of a flexible tube 66.

The apparatus 50 further comprises an oxygen sensor 68, located in the collection box 64, and a movement sensor provided by first and second switches 70, 72. The first switch 70 is embedded in the plunger 54. The second switch 72 is embedded in the wall of the housing 52, downstream of the gas outlet 62.

The oxygen sensor 68 and the switches 70, 72 are connected to a calculation means (not shown) by wires 74.

In use of the apparatus 50, the plunger 54 is arranged in the housing 52 at the start position as shown in FIG. 3.

A subject inhales external air through the opening 56 and the fluid inlet 60. The subject then exhales breath into the housing 52 via the fluid inlet 60.

The exhaled breath causes the plunger 54 to move away from the fluid inlet 60. The plunger 54 will continue to move in this direction until the end 76 of the plunger 54 passes the gas outlet 62 to reach the end position shown in FIG. 4. Thereafter, excess exhaled breath will pass out of the outlet 62 and into the collection box 64, and movement of the plunger 54 will cease.

During movement of the plunger 54 from the start position to the end position the switches 70, 72 measure the time taken to move this set distance. The measurement is sent to the calculation means (not shown) along wires 74.

The oxygen sensor 68 measures the oxygen content of the exhaled breath in the collection box 64, and sends the measurement to the calculation means (not shown) by means of wires 74.

The calculation means calculates the oxygen consumption in accordance with formula I set out above. The calculation is made in the same way as described above in relation to FIGS. 1 and 2.

Figure 5:
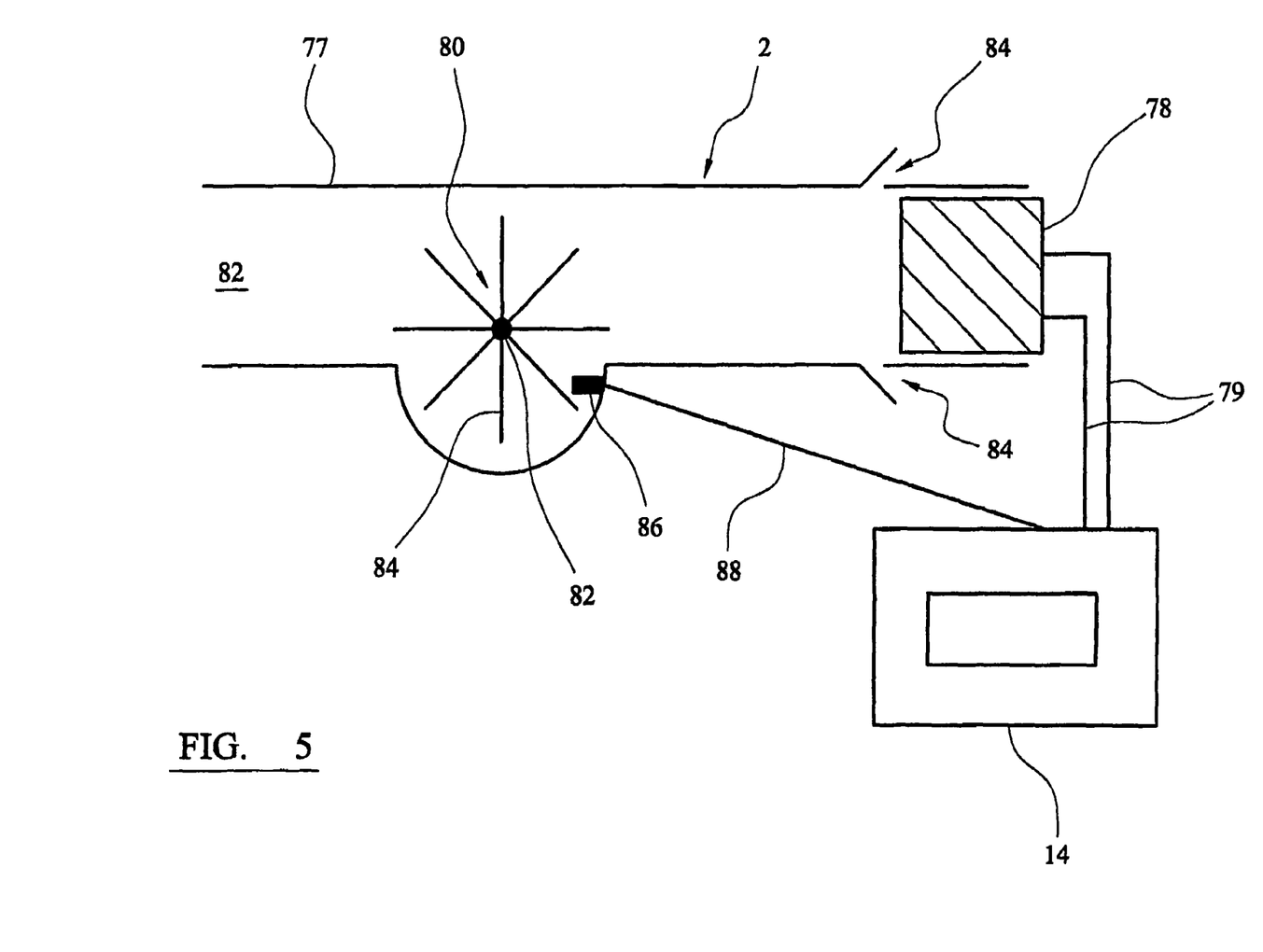
FIG. 5 is a schematic, partially cross-sectional side view of a second embodiment of a portable apparatus in accordance with the present invention.

We refer now to FIG. 5. FIG. 5 shows part of a portable apparatus for calculating respiratory oxygen consumption (2) comprising a housing (77), a rotor (80) comprising a rotor hub (82) from which extend eight rotor blades (84), an oxygen sensor (78) and a movement sensor provided by a first switch (86) mounted in the housing (77). The apparatus (2) further comprises electronic calculation means (14). The rotor (80) is mounted such that the rotor hub extends horizontally and perpendicular to the longitudinal direction of the housing (77). The rotor (80) is oriented such that the rotor blades (84) operably cooperate with the first switch (86) when the rotor rotates within the housing. Thus, each of the eight rotor blades (84) will sequentially operably cooperate with the first switch (86) as the rotor (80) rotates.

The housing (77) comprises a fluid inlet (82) and two fluid outlets in the form of vents (84). The fluid inlet is located at one end of the housing (77), with the vents (84) located at the other end thereof. The oxygen sensor (78) is embedded at the end of the housing (77) in which the vents (84) are located, downstream of the fluid inlet (82). The oxygen sensor (78) is electrically connected to electrical calculation means (14) by wires (79).

The first switch (86) is located in the housing (77), adjacent to the rotor (80), such that as the rotor rotates, the rotor blades (84) are arranged to move past the first switch (86) to thereby operably cooperate with the first switch (86). A wire (88) connects the first switch (86) to the electrical calculation means (14).

Use of the apparatus (2) of FIG. 5 will now be described. An exhaled breath is guided into the fluid inlet (82) of the housing (77). The end of the housing (77) providing the fluid inlet (82) may act as a mouthpiece for the apparatus (2). Alternatively, a separate mouthpiece (not shown) may be directly or indirectly connected to the housing (77). The exhaled breath causes the rotor (80) to rotate about the rotor hub (82), thereby causing rotational movement of the eight rotor blades (84) around the rotor hub (82). Whilst the rotor (80) is rotating, the oxygen sensor (78) measures the fraction of oxygen in the exhaled breath passing over the rotor blades (84) and to the oxygen sensor (78). The oxygen sensor (78) sends information of the measurement to the electrical calculation means (14) in the form of an electrical signal by means of wires (79).

During movement of the rotor (80), the first switch (86) measures the time taken between adjacent rotor blades (84) passing over the first switch (86) of the movement sensor. The first switch (86) also records information as to the total number of rotor blades (84) which pass the first switch (86) during an exhaled breath. The time taken between adjacent rotor blades (84) passing the first switch (86), and the total number of rotor blades (84) passing the first switch (86) is a measurement of the time taken to exhale a known volume of breath. The first switch (86) sends the measurement to the electrical calculation means (14) through the wire (88).

The electrical calculation means (14) is programmed to calculate the oxygen consumption of the subject in accordance with Formula I set out above. The calculation is made in the same way as described above in relation to FIGS. 1 and 2.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extend to any novel one, or any novel combination, of the features disclosed in this specification (including any accompanying claims, abstract and drawings), or to any novel one, or any novel combination, of the steps of any method or process so disclosed.

The invention claimed is:

1. A portable apparatus for calculating respiratory oxygen consumption comprising:
   a housing having a fluid inlet;
   a flow sensor mounted within the housing comprising a movable member movable by air pressure effected thereupon, and a movement sensor associated with the movable member wherein the movement sensor comprises one or more sensor switches;
   an oxygen sensor; and
   means for calculating the respiratory oxygen consumption using data obtained from the oxygen sensor and the flow sensor.

2. A portable apparatus according to claim 1, which is an indirect calorimeter.

3. A portable apparatus according to claim 1, wherein movement of the movable member within this housing is effected by passing a fluid into the housing through the fluid inlet.

4. A portable apparatus according to claim 3, wherein the fluid is exhaled breath.

5. A portable apparatus according to claim 1, wherein the oxygen sensor is mounted to the housing.

6. A portable apparatus according to claim 1, wherein the oxygen sensor is attached to an end of the movable member.

7. A portable apparatus according to claim 1, wherein the oxygen sensor is separate from the movable member.

8. A portable apparatus according to claim 1, wherein the movement sensor is arranged to measure the speed of movement of the movable member.

9. A portable apparatus according to claim 1, wherein a first switch is located on the movable member and a second switch is located on the housing.

10. A portable apparatus according to claim 1, wherein the movable member moves between a start position and an end position during use.

11. A portable apparatus according to claim 1, further comprising a fluid outlet.

12. A portable apparatus according to claim 11, wherein the fluid inlet is provided by an end of the housing.

13. A portable apparatus according to claim 1, wherein the movable member is a plunger slidably mounted within the housing, and wherein a fluid outlet is adjacent the end position of the plunger.

14. A portable apparatus according to claim 1, further comprising a collection chamber.

15. A portable apparatus according to claim 14, wherein the collection chamber is in fluid flow communication with a fluid outlet.

16. A portable apparatus according to claim 14, wherein the oxygen sensor is located in the collection chamber.

17. A portable apparatus according to claim 1, further comprising a mouthpiece associated with the fluid inlet.

18. A portable apparatus according to claim 1, wherein an opening in the housing allows external fluid to be inhaled through the apparatus by a subject using the apparatus.

19. A portable apparatus according to claim 1, wherein the movable member is a plunger slidably mounted within the housing, and wherein an opening in the housing that allows external fluid to be inhaled through the apparatus by the subject using the apparatus is located between the fluid inlet and the end of the plunger when the plunger is located in a start position.

20. A portable apparatus according to claim 18, further comprising a one-way-valve to seal the opening.

21. A portable apparatus according to claim 1, wherein the means for calculating the respiratory oxygen consumption comprises a computer or other electrical device.

22. A method of calculating respiratory oxygen consumption comprising the following steps:
   (a) passing an exhaled breath into a housing;
   (b) measuring the fraction of oxygen in the exhaled breath using an oxygen sensor;
   (c) measuring the time taken to exhale the breath using a flow sensor mounted within the housing; and
   (d) calculating the respiratory oxygen consumption using the data obtained in (b) and (c), wherein the calculation of respiratory oxygen consumption is carried out using the following formula:

$$VO_2 = K \times (F_iO_2 - F_eO_2) \times V \times (30/t) \times C \qquad \text{Formula I}$$

Where,
   $VO_2$ is the respiratory oxygen consumption of the subject,
   $F_iO_2$ is the fraction of inhaled oxygen,
   $F_eO_2$ is the fraction of exhaled oxygen,
   V is the volume of the exhaled breath over which the measurements are taken,
   t is the time taken to exhale the known volume of breath,
   C is the constant calorific value for oxygen, and
   K is a constant allowing for calibration.

23. A method as claimed in claim 22, wherein the flow sensor comprises a movable member associated with a movement sensor and step (a) comprises passing an exhaled breath into a housing to cause movement of the movable member.

24. A method according to claim 22, wherein step (a) comprises passing an exhaled breath of known volume into the housing.

25. A method according claim 22, wherein the method is carried out on a portable apparatus comprising:
   a portable apparatus for calculating respiratory oxygen consumption comprising;
   a housing having a fluid inlet;
   a flow sensor mounted within the housing;
   an oxygen sensors; and
   means for calculating the respiratory oxygen consumption using data obtained from the oxygen sensor and the flow sensor.

26. A method according claim 22, wherein steps (a) to (d) are repeated one or more times to obtain an average calculation of oxygen consumption.

* * * * *

UNITED STATES PATENT AND TRADEMARK OFFICE
CERTIFICATE OF CORRECTION

| | |
|---|---|
| PATENT NO. | : 7,060,036 B2 |
| APPLICATION NO. | : 10/467936 |
| DATED | : June 13, 2006 |
| INVENTOR(S) | : Austen Peter Bradley |

It is certified that error appears in the above-identified patent and that said Letters Patent is hereby corrected as shown below:

<u>Column 9, Claim 1</u>
Lines 8-12, delete the phrase:

"a movable member movable by air pressure effected thereupon, and a movement sensor associated with the movable member wherein the movement sensor comprises one or more sensor switches;"

and replace it with:

-- a plunger, slidably mounted within the housing, and movable by air pressure effected thereupon, and a movement sensor associated with the plunger; --

<u>Column 10, Claim 19</u>
Lines 1-3, delete the phrase:

"wherein the movable member is a plunger slidably mounted within the housing, and"

Signed and Sealed this

Seventh Day of November, 2006

JON W. DUDAS
*Director of the United States Patent and Trademark Office*